(12) United States Patent
Dewey et al.

(10) Patent No.: US 6,395,783 B1
(45) Date of Patent: May 28, 2002

(54) TREATMENT OF PCP ADDICTION AND PCP ADDICTION-RELATED BEHAVIOR

(75) Inventors: Stephen L. Dewey, Manorville, NY (US); Jonathan D. Brodie, Cos Cob, CT (US); Charles R. Ashby, Jr., Miller Place, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 0 days.

(21) Appl. No.: 09/694,040

(22) Filed: Oct. 23, 2000

(51) Int. Cl.$^7$ .................... A61K 31/195; A61K 31/165; A61K 31/135; A61K 31/4535

(52) U.S. Cl. .................... 514/561; 514/620; 514/638; 514/25

(58) Field of Search .................... 514/25, 326, 557, 514/561, 551, 620, 638

(56) References Cited

U.S. PATENT DOCUMENTS

| | | | |
|---|---|---|---|
| 4,540,582 A | 9/1985 | Seiler et al. ................. | 514/561 |
| 4,595,697 A | 6/1986 | Seiler et al. ................. | 514/534 |
| 4,621,145 A | 11/1986 | Frieben et al. ............... | 548/543 |
| 5,102,913 A | * 4/1992 | Halikas ........................ | 514/557 |
| 5,189,064 A | 2/1993 | Blum et al. .................. | 514/561 |

FOREIGN PATENT DOCUMENTS

| | | |
|---|---|---|
| WO | WO 89 03211 A | 4/1989 |
| WO | WO 99/21540 | 5/1999 |
| WO | WO 00/50020 | 8/2000 |

OTHER PUBLICATIONS

Morgan et al., "Longterm Cocaine Adminstration May Alter Specific Gabaergic Pathways", *Abstracts Society for Neuroscience*, 23:1942 (1997).

Kushner et al., "Comparison of the Effects of Vigabatrin on Cocaine Self–Administration and Food Reinforcement", *Abstracts Society for Neuroscience*, 23:1942 (1997).

Dewey et al., "GABAergic Attenuation of Cocaine–Induced Dopamine Release and Locomotor Activity", *Synapse*, 25:393–398 (1997).

Morgan et al., "Effects of Pharmacologic Increases in Brain GABA Levels on Cocaine–Induced Changes in Extracellular Dopamine", *Synapse* 28:60–65 (1998).

Kushner et al., "Gamma–vinyl GABA Attenuates Cocaine–Induced Lowering of Brain Stimulation Reward Thresholds", *Psychopharmacology*, 133:383–388 (1997).

Porter et al., "Antiepileptic Drugs", *Basic and Clinical Pharmacology*, ed. by Katzung, B.G., Appelton and Lange, Stamford, CT pp. 386–408 (1998).

Takada et al., "Drug Dependence Study on Vigabatrin in Rhesus Monkeys and Rats", *Arzneim.–Forsch Drug Res* 47(II), 1087–1092 (1997).

Nisell et al., "Nicotine Dependence, Midbrain Dopamine Systems and Psychiatric Disorders", *Pharmacology & Toxicology*, 76:157–162 (1995).

Nisell et al., "Infusion of Nicotine in the Ventral Tegmental Area or the Nucleus Accumbens of the Rat Differentially Affects Accumbal Dopamine Release", *Pharmacology & Toxicology*, 75:348–352 (1994).

Fudala et al., "Pharmacologic Characterization of Nicotine–Induced Conditioned Place Preference", *Pharmacol Biochem Behav* 22(2) 237–241 (1985).

Clarke et al., "Apparent Absence of Nicotine–Induced Conditioned Place Preference in Rats" *Psychopharmacology* 92: 84–88 (1987).

Clarke et al., "Evidence That Mesolimbic Dopaminergic Activation Underlies the Locomotor Stimulant Action of Nicotine in Rats", *The Journal of Pharmacology and Experimental Therapeutics*, 246:701–708 (1988).

Henningfield et al., "Control of Behavior by Intravenous Nicotine Injections in Human Subjects", *Pharmacology Biochemistry & Behavior*, 19:1021–1026 (1983).

Jarvik et al., "Pharmacological Treatment of Tobacco Dependence", *Pharmacology Biochemistry & Behavior*, 30:279–294 (1988).

Henningfield et al., "Cigarette Smokers Self–Administer Intravenous Nicotine", *Pharmacology Biochemistry & Behavior* 19:887–890 (1983).

Nisell et al., "Systemic Nicotine–Induced Dopamine Release in the Rat Nucleus Accumbens is Regulated by Nicotinic Receptors in the Ventral Tegmental Area", *Synapse* 16:36–44 (1994).

Pontieri et al., "Effects of nicotine on the nucleus accumbens and similarity to those of addictive drugs" *Nature* 382:255–257 (1996).

Di Chiara et al., "Drugs Abused by Humans Preferentially Increase Synaptic Dopamine Concentrations in the Mesolimbic System of Freely Moving Rats", *Proc. Natl. Acad. Sci. USA*, 85:5274–5278 (1988).

Damsma et al., "Lack of Tolerance to Nicotine–Induced Dopamine Release in the Nucleus Accumbens", *European Journal of Pharmacology*, 168:363–368 (1989).

Imperato et al., "Nicotine Preferentially Stimulates Dopamine Release in the Limbic System of Freely Moving Rats", *European Journal of Pharmacology*, 132:337–338 (1986).

(List continued on next page.)

Primary Examiner—Phyllis G. Spivack
(74) Attorney, Agent, or Firm—Margaret C. Bogosian

(57) ABSTRACT

The present invention provides a method for changing addiction-related behavior of a mammal suffering from addiction to phencyclidine (PCP). The method includes administering to the mammal an effective amount of gamma vinylGABA (GVG) or a pharmaceutically acceptable salt thereof, or an enantiomer or a racemic mixture thereof, wherein the effective amount is sufficient to diminish, inhibit or eliminate behavior associated with craving or use of PCP.

33 Claims, 1 Drawing Sheet

OTHER PUBLICATIONS

Figure 1:
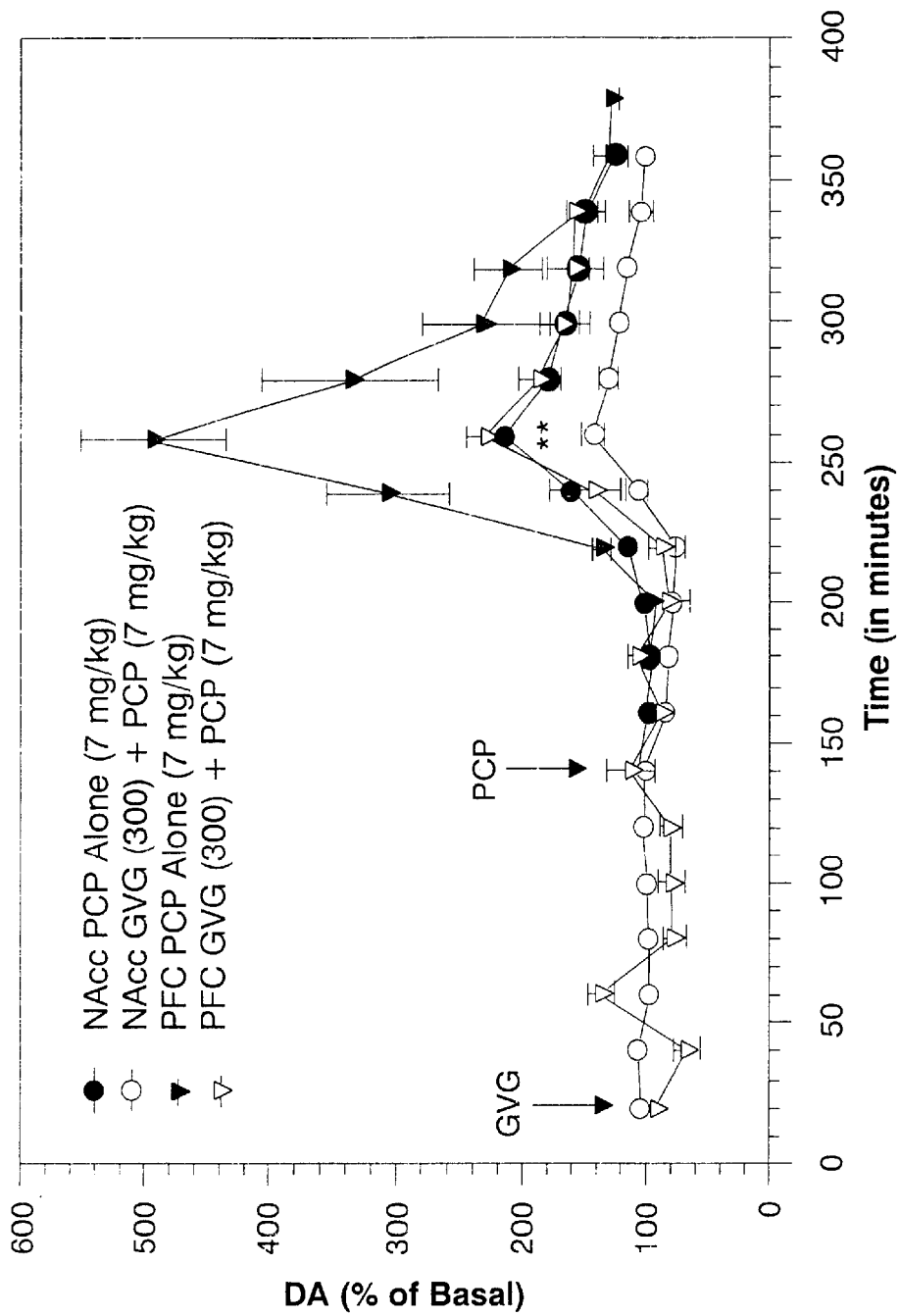

Brazell et al., "Acute Administration of Nicotine Increases the In Vivo Extracellular Levels of Dopamine, 3,4–Dihydroxyphenylacetic Acid and Ascorbic Acid Preferentially in the Nucleus Accumbens of the Rat: Comparison with Caudate–Putamen", *Neuropharmacology* 29:1177–1185 (1990).

Horan et al., "Nicotine Produces Conditioned Place Preference in Lewis But Not Fischer 344 Rats", *Synapse* 26:93–94 (1997).

Lepore et al., "Conditioned Place Preference Induced By $^9$–Tetrahydrocannabinol: Comparison with Cocaine, Morphine, and Food Reward", *Life Sciences,* 56:2073–2080 (1995).

Sora et al., "Cocaine reward models: conditioned place preference can be established in dopamine–and in serotonin–transporter knockout mice" *Proc. Natl. Acad. Sci. USA* 95:7699–7704 (1998).

Valentine et al., "Self–Adminstration in Rats Allowed Unlimited Access to Nicotine" *Psychopharmacology,* 133:300–305 (1997).

Eliot L. Gardner, "6 Brain Reward Mechanisms", *Substance Abuse: A Comprehensive Textbook,* p.51–85 (1997).

Marshall et al., "Presynaptic Nicotinic Modulation of Dopamine Release in the Three Ascending Pathways Studied by In Vivo Microdialysis: Comparison of Naive and Chronic Nicotine–Treated Rats" *Journal of Neurochemistry,* 68:1511–1519 (1997).

M.–F. Chesselet, "Presynaptic Regulation of Neurotransmitter Release in the Brain", *Neuroscience* 12:347–375 (1984).

Lacey et al., "On the Potassium Conductance Increase Activated by $GABA_B$ and Dopamine $D_2$ Receptors in Rat Substantia Nigra Neurones" *Journal of Physiology* 401:437–453 (1988).

Grant et al., "Vigabatrin: A Review of its Pharmacodynamic an Pharmacokinetic Properties, and Therapeutic Potential in Epilepsy and Disorders of Motor Control" *Drugs* 41 6:889–926 (1991).

Jung et al., "Vinyl GABA (4–amino–hex–5–enoic acid). A New Selective Irreversible Inhibitor of GABA–T: Effects on Brain GABA Metabolism in Mice" *Neurochem.* 29:797–802 (1977).

Tsuji et al., "Activation of Ventral Tegmental $GABA_{+sc\ B}$ Receptors Inhibits Morphine–Induced Place Preference in Rats" *European Journal of Pharmacology* 313:169–173.

Roberts et al., "Baclofen Suppression of Cocaine Self–Adminstration: Demonstration Using a Discrete Trials Procedure" *Psychopharmacology* 131:271–277 (1997).

Bolser et al., "The Pharmacology of SCH 50911: A Novel, Orally–Active GABA–B Receptor Antagonist" *The Journal of Pharmacology and Experimental Therapeutics* 274:1393–1398 (1995).

Roberts et al., "Baclofen Attenuates the Reinforcing Effects of Cocaine in Rats" *Neuropsychopharmacology* 15:417–423 (1996).

Derek van der Kooy, "Place Conditioning: A Simple and Effective Method for Assessing the Motivational Properties of Drugs" *M.A. Bozarth, Ed., Springer–Verlag, New York,* pp. 229–241 (1987).

Hurt et al., "A Comparison of Sustained–Release Bupropion and Placebo for Smoking Cessation" *The New England Journal of Medicine* 337:1195:1202 (1997).

Volkow et al., "Imaging Endogenous Dopamine Competition With [$^{11}$C] Raclopride in the Human Brain" *Synapse* 16:255–262 (1994).

Logan et al., "Graphical Analysis of Reversible Radioligand Binding from Time–Activity Measurements Applied to [N–$^{11}$C–Methyl]–(–)–Cocaine PET Studies in Human Subjects" *Journal of Cerebral Blood Flow and Metabolism* 10:740–747 (1990).

Dewey et al., "A Novel Strategy for the Treatment of Cocaine Addiction" *Synapse* 30:119–129 (1998).

Dewey et al., "Striatal Binding of the PET Ligand $^{11}$C–Raclopride is Altered by Drugs that Modify Synaptic Dopamine Levels" *Synapse* 13:350–356 (1993).

Dewey et al., "GABAergic Inhibition of endogenous Dopamine Release Measured in vivo with $^{11}$C–Raclopride and Positron Emission Tomography" *The Journal of Neuroscience* 12(10):3773–3780 (1992).

Dewey et al., "Effects of Central Cholinergic Blockade on Stratial Dopamine Release Measured with Positron Emission Tomography in Normal Human Subjects" *Proc. Natl. Acad. Sci. USA* 90:11816–11820 (1993).

Buckland et al., "Amphetamine and Vigabatrin Down Regulate Aromatic L–amino acid Decarboxylase mRNA levels" *Molecular Brain Research* 35:69–76 (1996).

Cubells et al., "In Vivo Action of Enzyme–Activated Irreversible Inhibitors of Glutamic Acid Decarboxylase and —Aminobutyric Acid Transaminase in Retina vs. Brain" *The Journal of Pharmacology and Experimental Therapeutics* 238:508–514 (1986).

Herbert D. Kleber, "Treatment of Cocaine Abuse: Pharmacotherapy" *Cocaine Scientific and Social Dimensions* p.195–206 (1992).

Sherif et al., "Basic Aspects of GABA–transmission in Alcoholism, with Particular Reference to GABA–transaminase" *European Neuropsychopharmacology* 7:1–7(1997).

Dewey et al., "A New GABAergic strategy for treating cocaine addiction" *J. Nuclear Med.* 39:99–100 (1998).

Morgan et al., "Vigabatrin Attenuates Cocaine–Induced Changes in Brian Dopamine Concentrations" *J. Nuclear Med.* 38:11p (1997).

Kushner et al., The irreversible Gamma–aminobutyric acid (GABA) transaminase inhibitor Gamma–vinyl–GABA blocks cocaine self–administration in rats *J. Pharmacology and Experimental Therapeutics* 290:797–802 (1999).

Dewey et al., "A Pharmacologic Strategy for the Treatment of Nicotine Addiction" *Synapse* 31:76–86 (1999).

Midgley et al., Brain Research, 593/1, pp. 89–96, 1992.*

Giannini et al., American Family Physician, 40(5), pp. 173–182 (Nov., 1989).*

Beardsley et al., Psychopharmacology, 127(4), pp.315–322 (Oct., 1996) (abstract).*

* cited by examiner

TREATMENT OF PCP ADDICTION AND PCP ADDICTION-RELATED BEHAVIOR

This invention was made with Government support under contract number DE-AC02-98CH10886, awarded by the U.S. Department of Energy. The Government has certain rights in the invention.

BACKGROUND OF THE INVENTION

This invention relates to the use of an irreversible inhibitor of GABA-transaminase for the treatment of substance addiction and modification of behavior associated with substance addiction. More specifically, the invention relates to the treatment of phencyclidine addiction and modification of behavior associated with phencyclidine addiction.

Phencyclidine, better known as PCP, is an illegal synthetic drug. Unlike cocaine and THC which are derived from natural sources, PCP is made from industrial chemicals.

PCP was developed in the 1950's as an intravenous anesthetic. Use of PCP in humans was discontinued in 1965, because it was found that patients often became agitated, delusional and irrational while recovering from its anesthetic effects. PCP is illegally manufactured in laboratories and is sold on the street by such names as "angel dust", "ozone", "wack", and "rocket fuel". "Killer joints" and "crystal supergrass" are names that refer to PCP combined with marijuana. The variety of street names for PCP reflects its bizarre and volatile effects.

PCP is a white crystalline powder that is readily soluble in water or alcohol. It has a distinctive bitter chemical taste. PCP can be mixed easily with dyes and turns up on the elicit drug market in a variety of tablets, capsules, and colored powders. It is normally used in one of three ways: snorted, smoked, or ingested. For smoking, PCP is often applied to a leafy material such as mint, parsley, oregano or marijuana.

PCP interrupts the functions of the neocortex, the section of the brain that controls the intellect and keeps instincts in check. Because the drug blocks pain receptors, violent PCP episodes may result in self-inflicted injuries. The effects of PCP vary, but users frequently report a sense of distance and estrangement. Time and body movements are slowed down. Muscular coordination worsens and senses are dulled. Speech is blocked and incoherent. In later stages of chronic use, users often exhibit paranoid and violent behavior and experience hallucinations. Large doses may produce convulsions and coma, as well as heart and lung failure.

PCP is addicting. There is evidence of both physical and psychological dependence upon PCP. Use of PCP often leads to psychological dependence, craving, and compulsive PCP-seeking behavior.

Many PCP users are brought to emergency rooms because of PCP's adverse psychological effects or because of overdoses. In a hospital or detention setting, PCP users often become violent or suicidal, and are very dangerous to themselves and to others.

At low to moderate doses, physiological effects of PCP include a slight increase in breathing rate and a more pronounced rise in blood pressure and pulse rate. Respiration becomes shallow, and flushing and profuse sweating occur. Generalized numbness of the extremities and muscular incoordination also may occur. The psychological effects include distinct changes in body awareness, similar to those associated with alcohol intoxication. Use of PCP among adolescents may interfere with hormones related to normal growth and development as well as the learning process.

At high doses of PCP, there is a drop in blood pressure, pulse rate, and registration. This may be accompanied by nausea, vomiting, blurred vision, flicking up and down of the eyes, drooling, loss of balance, and dizziness. High doses of PCP can also cause seizures, coma and death. The psychological effects at high doses include illusions and hallucinations. PCP can cause effects that mimic the full range of symptoms of schizophrenia, such as delusions, paranoia, disordered thinking, a sensation of distance from ones' environment, and catatonia. Speech is often sparse and garbled.

People who use PCP for long periods report memory loss, difficulties with speech and thinking, depression and weight loss. These symptoms can persist up to a year after sustained PCP use. Mood disorders also have been reported. PCP has sedative effects, and interactions with other central nervous system depressants, such as alcohol and benzodiazepines, can lead to coma or accidental overdose.

It has been found that addicting drugs such as nicotine, cocaine and PCP enhance dopamine (DA) within the mesotelencephalic reward/reinforcement circuitry of the forebrain, presumably producing the enhanced brain reward that consisutes the drug user's "high". Alterations in the functions of the dopamine (DA) systems have also been implicated in drug craving and in relapse to the drug-taking habit in recovering addicts. For example, cocaine acts on these DA systems by binding to the dopamine transporter (DAT) and preventing DA reuptake into the presynaptic terminal. There is considerable evidence that the addictive liability of addicting drugs is linked to the reuptake blockade in central nervous system (CNS) reward/reinforcement pathways.

There are currently no medications approved by the food and drug administration (FDA) for treating addiction to PCP. There are medications, however, for treating the adverse health effects of using PCP. Generally, there are two types of medications that are used to treat PCP abuse. They are anti-anxiety medications such as diazeparn, better known as Valium®. Anti-anxiety medications are administered when the PCP user experiences delusional symptoms, hallucinations, or feels paranoid. However, such medications only treat the symptoms as opposed to the addiction itself.

Thus, there remains a need in the treatment of addiction to PCP which can relieve a patient's craving by changing the pharmacological actions of PCP in the central nervous system.

SUMMARY OF THE PRESENT INVENTION

The present invention, which addresses the needs of the prior art, provides methods for treating substance addiction and changing addiction-related behavior of a mammal, for example a primate, suffering from phencyclidine (PCP) addiction by administering to the mammal an effective amount of a pharmaceutical composition or medicament which includes gamma vinyl GABA (GVG). The amount of GVG varies from about 15 mg/kg to about 2 gm/kg, preferably from about 100 mg/kg to about 600 mg/kg, and most preferably from about 150 mg/kg to about 300 mg/kg.

In another embodiment, the present invention provides a method for changing addiction-related behavior of a mammal suffering from addiction to PCP which comprises administering to the mammal an effective amount of GVG or a pharmaceutically acceptable salt thereof, wherein the effective amount attenuates the rewarding/incentive effects of PCP in the absence of altering rewarding/incentive effects of food in said mammal.

The amount of GVG varies from about 15 mg/kg to about 2 gm/kg, preferably from about 15 mg/kg to about 600 mg/kg, and most preferably from about 150 mg to about 600 mg/kg.

As a result of the present invention, methods of reducing PCP addiction and changing addiction-related behavior are provided which are based on a pharmaceutical composition or medicament which is not itself addictive, yet is highly effective in reducing the addiction and the addictive behavior of addicted patients. The pharmaceutical composition or medicament useful for the method of the present invention inhibits or eliminates craving experienced by PCP addicts. Moreover, the reduction of behavior associated with PCP addiction occurs in the absence of an aversive or appetitive response to GVG. Moreover, behavior characteristics associated with dependency on PCP are reduced or eliminated in the absence of an alteration in the locomotor function of the primate.

In yet another embodiment, the invention includes a method for changing addiction-related behavior of a mammal suffering from addiction to PCP which comprises administering to the mammal an effective amount of GVG or a pharmaceutically acceptable salt thereof, or an enantiomer or a racemic mixture thereof, wherein the effective amount is sufficient to diminish, inhibit or eliminate behavior associated with craving or use of PCP.

In another exemplary embodiment of the present invention, the method includes changing addiction-related behavior of a mammal suffering from addiction to PCP which comprises administering to the mammal an effective amount of a composition or medicament that increases central nervous system GABA levels, wherein the effective amount is sufficient to diminish, inhibit or eliminate behavior associated with craving or use of PCP.

Other improvements which the present invention provides over the prior art will be identified as a result of the following description which sets forth the preferred embodiments of the present invention. The description is not in any way intended to limit the scope of the present invention, but rather only to provide a working example of the present preferred embodiments. The scope of the present invention will be pointed out in the appended claims.

BRIEF DESCRIPTIONS OF THE DRAWINGS

FIG. 1 is a graph illustrating the effect of GVG on PCP-induced DA release in the nucleus accumbens (Nacc) and prefrontal cortex (PFC).

DETAILED DESCRIPTION OF THE INVENTION

The present invention provides a highly efficient method for treating PCP addiction and for changing PCP addiction-related behavior of primates, for example mammals.

As used herein, addiction-related behavior means behavior resulting from compulsive PCP use and is characterized by apparent dependency on the substance. Symptomatic of the behavior is (i) overwhelming involvement with PCP, (ii) the securing of its supply, and (iii) a high probability of relapse after withdrawal.

PCP addiction is defined herein to include PCP addiction together with addiction to other drugs of abuse. Drugs of abuse include but are not limited to psychostimulants, narcotic analgesics, alcohols and addictive alkaloids such as nicotine or combinations thereof. Drugs of abuse also include CNS depressants such as barbiturates, chlordiazepoxide, and alcohols such as ethanol, methanol and isopropyl alcohol.

Compulsive drug use includes three independent components: tolerance, psychological dependence, and physical dependence. Tolerance produces a need to increase the dose of the drug after it is used several times in order to achieve the same magnitude of effect. Physical dependence is an adaptive state produced by repeated drug administration and which manifests itself by intense physical disturbance when drug administration is halted. Psychological dependence is a condition characterized by an intense drive, craving or use for a drug whose effects the user feels are necessary for a sense of well being. See Feldman, R. S. and Quenzer, L. F. "Fundamentals of Neuropsychopharmocology" 418–422 (Sinaur Associates, Inc.) (1984) incorporated herein by reference as if set forth in full. Based on the foregoing definitions, as used herein "dependency characteristics" include all characteristics associated with compulsive drug use, characteristics that can be affected by biochemical composition of the host, physical and psychological properties of the host.

As used herein the rewarding/incentive effects of PCP refers to any stimulus (in this case, a drug) that produces anhedonia or increases the probability of a learned response. This is synonymous with reinforcement. With respect to experimental animals, a stimulus is deemed to be rewarding by using paradigms that are believed to measure reward. This can be accomplished by measuring whether stimuli produce an approach response, also known as an appetitive response or a withdrawal response, as when the animal avoids the stimuli, also known as an aversive response. Conditioned place preference (CPP) is a paradigm which measures approach (appetitive) or withdrawal (aversive) responses. One can infer that rewarding stimuli produce approach behavior. In fact, one definition of reward is any stimulus that elicits approach behavior. Furthermore, the consequences of reward would be to enhance the incentive properties of stimuli associated with the reward.

Reward can also be measured by determining whether the delivery of a reward is contingent upon a particular response, thereby increasing the probability that the response will reappear in a similar situation, i.e. reinforcement paradigm. For example, a rat pressing a bar a certain number of times for an injection of a drug is an example of reinforcement. Yet another way to measure reward is by determining if a stimulus (e.g. a drug), through multiple pairings with neutral environmental stimuli, can cause the previously neutral environmental stimuli to elicit behavioral effects initially only associated with the drug. This is conditioned reinforcement. CPP is considered to be a form of conditioned reinforcement.

The incentive motivational value of a drug can be assessed using conditioned place preference (CPP). Animals are tested in a drug-free state to determine whether they prefer an environment in which they previously received the drug as compared to an environment in which they previously received saline. In the CPP paradigm, animals are given the drug in one distinct environment and are given the appropriate vehicle in an alternative environment. The CPP paradigm is widely used to evaluate the incentive motivational effects of drugs in laboratory animals (Van Der Kooy, 1995). After conditioning or pairing with the drug, if the animal, in a drug-free state, consistently chooses the environment previously associated with the drug; the inference is drawn that the appetitive value of the drug was encoded in the brain and is accessible in the drug-free state. CPP is reflected in an increased duration spent in the presence of the drug-associated stimuli relative to vehicle-injected control animals.

It has been postulated that since craving at the human level is often elicited by sensory stimuli previously associated with drug-taking, conditioning paradigms like CPP may be used to model craving in laboratory animals.

As used herein, craving an abused drug or a combination of abused drugs is a desire to self-administer the drug(s) previously used by the mammal. The mammal does not necessarily need the abused drug to prevent withdrawal symptoms.

The addictive liability of PCP has been linked to its pharmacological actions on mesotelencephalic dopamine (DA) reinforcement/reward pathways in the central nervous system (CNS). Dopaminergic transmission within these pathways is modulated by gamma-amino butyric acid (GABA).

PCP inhibits the presynaptic reuptake of monoamines. Dopaminergic neurons of the mesocorticolimbic DA system, whose cell bodies lie within the ventral tegmental area (VTA) and project primarily to the nucleus accumbens (NAcc), appear to be involved in PCP reinforcement. Electrical stimulation of reward centers within the VTA increases extracellular DA levels in the NAcc, while 6-hydroxy dopamine lesions of the NAcc abolish PCP self-administration. In vivo microdialysis studies confirm PCP's ability to increase extracellular DA in the NAcc.

γ-Amino butyric acid (GABA)ergic neurons in the NAcc and ventral pallidum project onto DA neurons in the VTA. Pharmacologic and electrophysiologic studies indicate these projections are inhibitory. Inhibition of VTA-DA neurons is likely the result of $GABA_B$ receptor stimulation. In addition, microinjection of baclofen into the VTA, acting via these receptor subtypes, can decrease DA concentrations in the NAcc. Taken together, it is evident that pharmacologic manipulation of GABA may effect DA levels in the NAcc through modulation of VTA-DA neurons. Gamma Vinyl GABA Gamma vinyl GABA (GVG) is a selective and irreversible inhibitor of GABA-transaminase (GABA-T) known to potentiate GABAergic inhibition. GVG is $C_6H_{11}NO_2$ or 4-amino -5-hexanoic acid available as VIGABATRIN® from Hoechst Marion Roussel and can be obtained from Marion Merell Dow of Cincinnati, Ohio. GVG does not bind to any receptor or reuptake complex, but increases endogenous intracellular GABA levels by selectively and irreversibly inhibiting GABA-transaminase (GABA-T), the enzyme that normally catabolizes GABA.

As used herein GVG includes the racemic compound or mixture which contains equal amounts of S(+)-gamma-vinyl GABA, and R(−)-gamma vinyl GABA. This racemic compound of GVG is available as SABRIL® from Aventis Pharma AG.

GVG contains asymmetric carbon atoms and thus is capable of existing as enantiomers. The present invention embraces any enantiomeric form of GVG including the racemates or racemic mixture of GVG. In some cases there may be advantages, i.e. greater efficacy, to using a particular enantiomer when compared to the other enantiomer or the racemate or racemic mixture in the methods of the instant invention and such advantages can be readily determined by those skilled in the art. For example, the enantiomer S(+)-gamma-vinyl GABA is more effective at increasing endogenous intracellular GABA levels than the enantiomer R(−)-gamma-vinyl GABA.

Different enantiomers may be synthesized from chiral starting materials, or the racemates may be resolved by conventional procedures which are well known in the art of chemistry; such as chiral chromatography, fractional crystallization of diastereomeric salts, and the like.

Administration of Gamma Vinyl GABA

In living mammals (in vivo), GVG or pharmaceutically acceptable salts thereof, can be administered systemically by the parenteral and enteral routes which also includes controlled release delivery systems. For example, GVG can easily be administered intravenously, or intraperitoneal (i.p.) which is a preferred route of delivery. Intravenous or intraperitoneal administration can be accomplished by mixing GVG in a suitable pharmaceutical carrier (vehicle) or excipient as understood by practitioners in the art.

Oral or enteral use is also contemplated, and formulations such as tablets, capsules, pills, troches, elixirs, suspensions, syrups, wafers, chewing gum and the like can be employed to provide GVG or pharmaceutically acceptable salts thereof.

As used herein, pharmaceutically acceptable salts include those salt-forming acids and bases which do not substantially increase the toxicity of the compound. Some examples of suitable salts include salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g. p-toluenesulfonic acids, and the like.

An effective amount as used herein is that amount effective to achieve the specified result of changing addiction-related behavior of the mammal. It is an amount which will diminish or relieve one or more symptoms or conditions resulting from cessation or withdrawal of the drug. It should be emphasized, however, that the invention is not limited to any particular dose.

Mammals include, for example, humans, baboons and other primates, as well as pet animals such as dogs and cats, laboratory animals such as rats and mice, and farm animals such as horses, sheep, and cows.

Preferably, GVG is administered in an amount which has little or no adverse effects. For example, to treat PCP addiction, GVG is administered in an amount of from about 15 mg/kg to about 2 g/kg, preferably from about 100 mg/kg to about 300 mg/kg or from about 15 mg/kg to about 600 mg/kg and most preferably from about 150 mg/kg to about 300 mg/kg or from about 75 mg/kg to about 150 mg/kg.

Based on the knowledge that PCP increases extracellular NAcc DA and the fact that GABA inhibits DA in the same nuclei, we have shown that GVG can attenuate PCP-induced changes in extracellular DA. For example, GVG significantly attenuated PCP-induced increases in neostriatal synaptic DA in the primate (baboon) brain as assessed by positron emission tomography (PET).

These findings suggest the possible therapeutic utility in PCP addiction of a pharmacologic strategy targeted at the GABAergic neurotransmitter system, a system distinct from but functionally linked to the DA mesotelencephalic reward/reinforcement system. However, rather than targeting the GABA receptor complex with a direct GABA agonist, this novel approach with GVG takes advantage of the prolonged effects of an irreversible enzyme inhibitor that raises endogenous GABA levels without the addictive liability associated with GABA agonists acting directly at the receptor itself.

Although GVG is used in the present examples, it will be understood by those skilled in the art that other compositions or medicaments can be used which are known to potentiate the GABAergic system or increase extracellular endogenous GABA levels in the CNS. Such compositions or medicaments include drugs that enhance the production or release of GABA in the CNS. These drugs include, but are not limited to, gabapentin, valproic acid, progabide, gamma-hydroxybutyric acid, fengabine, cetylGABA, topiramate, tiagabine, acamprosate (homo-calcium-acetyltaurine) or a pharmaceutically acceptable salt thereof, or an enantiomer or a racemic mixture thereof.

The present invention embraces any enantiomeric form of gabapentin, valproic acid, progabide, gamma-hydroxybutyric acid, fengabine, cetylGABA, topiramate, tiagabine, or acamprosate, including the racemates or racemic mixtures thereof.

As previously stated, in some cases there may be advantages, i.e. greater efficacy, to using a particular enantiomer when compared to the other enantiomer or the racemate or racemic mixture in the methods of the instant invention and such advantages can be readily determined by those skilled in the art.

The present invention embraces compositions or medicaments which include prodrugs of GABA or drugs which contain GABA as a moiety in its chemical structure. These prodrugs become pharmacologically active when metabolically, enzymatically or non-enzymatically biotransformed or cleaved into GABA in the CNS. An example of a prodrug of GABA is progabide which, upon crossing the blood brain barrier, increases endogenous CNS GABA levels.

As previously stated, Gamma vinyl GABA (GVG) is a selective and irreversible inhibitor of GABA-transaminase (GABA-T) known to potentiate GABAergic inhibition. Other compositions or medicaments which inhibit GABA re-uptake in the CNS are also encompassed by the present invention. An example of a GABA re-uptake inhibitor is tiagabine.

The method of the present invention is useful in potentiating the GABAergic system or increasing extracellular endogenous GABA levels in the CNS. As used herein, enhancing or increasing endogenous CNS GABA levels is defined as increasing or up-regulating GABA levels substantially over normal levels in vivo, within a mammal. Preferably, endogenous CNS GABA levels are enhanced at least by from about 10% to about 600% over normal levels.

As previously stated, an effective amount as used herein is that amount effective to achieve the specified result of changing addiction-related behavior of the mammal. It is an amount which will diminish or relieve one or more symptoms or conditions resulting from cessation or withdrawal of PCP. It should be emphasized, however, that the invention is not limited to any particular dose.

For example, an effective amount of gabapentin administered to the mammal is an amount from about 500 mg to about 2 g/day. Gabapentin is available as NEUROTONIN® from Parke-Davis in the United States.

An effective amount of valproic acid administered to the mammal, for example, is preferably an amount from about 5 mg/kg to about 100 mg/kg/day. Valproic acid is available as DEPAKENE® from Abbott in the United States.

Preferably, an effective amount of topiramate administered to the mammal is, for example, an amount from about 50 mg to about 1 g/day. Topiramate is available as TOPAMAX® from McNeil in the United States. An effective amount of progabide administered to the mammal is, preferably, an amount from about 250 mg to about 2 g/day. Progabide is available as GABRENE® from Synthelabo, France. The chemical formula of progabide is $C_{17}H_{16}N_2O_2$.

An effective amount of fengabine administered to the mammal is, preferably, an amount from about 250 mg to about 4 g/day. Fengabine is available as SL 79229 from Synthelabo, France. The chemical formula of fengabine is $C_{17}H_{17}C_{12}NO$.

Preferably, an effective amount of gamma-hydroxybutyric acid administered to the mammal is an amount from about 5 mg/kg to about 100 mg/kg/day. Gamma-hydroxybutyric acid is available from Sigma Chemical. The chemical formula of gamma-hydroxybutyric acid is $C_4H_7O_3Na$.

Details of the invention have been set forth herein in the form of examples which are described below. The full scope of the invention will be pointed out in the appended claims.

EXAMPLE 1

We explored the effects of increased endogenous GABA activity on PCP-induced extracellular DA concentrations in the prefrontal cortex (PFC) and nucleus accumbens (NAcc) of freely moving rats.

All animals were used under an IACUC-approved protocol and with strict adherence to the NIH guidelines. Adult male Sprague-Dawley rats (200–300 g, Taconic Farms), housed in the animals care facility under 12:12 light/dark conditions, were placed into 6 groups (n=3–6), anesthetized and siliconized guide cannulae were stereotactically implanted into the right NAcc (2.0 mm anterior and 1.0 mm lateral to bregms, and 7.0 mm ventral to the cortical surface) and prefrontal cortex (PFC) at least 4 days prior to study. Microdialysis probes (2.0 mm, Bioanalytical Systems, BAS, West Lafayette, Ind.) were positioned within the guide cannulae and artificial cerebrospinal fluid (ACSF, 155.0 mM NA$^-$, 1.1 mM Ca$^{2-}$, 2.9 mM K$^-$, 132.76 mM Cl$^{31}$, and 0.83 mM Mg$^{2-}$) was administered through the probe using a CMA/100 microinfusion pump (BAS) at a flow rate of 2.0 $\mu$/min.

Animals were placed in bowls, and probes were inserted and flushed with ACSF overnight. On the day of the study, a minimum of three samples were injected to determine baseline stability. Samples were collected for 20 min. and injected on-line (CMA/160, BAS). The average dopamine concentration of these three stable samples was defined as control (100%), and all subsequent treatment values were transformed to a percentage of that control. Upon establishing a stable baseline, the PCP was administered by intraperitoneal (i.p.) injection. The high performance liquid chromatography (HPLC) system consists of a BAS reverse-phase column (3.0$\mu$ C-18), a BAS LC-4C electrochemical transducer with a dual/glassy carbon electrode set at 650 mV, a computer that analyzes data on-line using a commercial software package (Chromograph Bioanalytical Systems), and a dual pen chart recorder. The mobile phase (flow rate 1.0 ml/min) consisted of 7.0% methanol, 50 mM sodium phosphate monobasic, 1.0 mM sodium octyl sulfate, and 0.1 mm EDNA, pH 4.0. DA eluted at 7.5 min.

Gamma-vinyl GABA (GVG), an irreversible inhibitor of GABA-transaminase, was administered by intraperitoneal injection 2.5 hours prior to PCP (7 mg/kg). In all studies, animals were placed in the microdialysis bowls the night before the experiment and artificial cerebrospinal fluid (ACSF) was perfused through the microdialysis probes at a flow rate of 2.0 $\mu$l/min. At the end of each study, animals were sacrificed and their brains were removed and sectioned for probe placement verification.

Levels of extracellular DA were sampled from the NAcc continuously using a stereoaxically implanted probe. The results are shown in FIG. 1 (PCP Controls, n=6; 150 mg/kg GVG, n=3; 300 mg/kg GVG, n=4 and 500 mg/kg GVG, n=4) and PFC (PCP Controls, n=5; 300 mg/kg GVG, n=5). PCP alone increases DA concentrations 407% above baseline in the PFC and 117% in the NAcc (p<0.01, T=3.79). GVG dose dependently diminished the DA response to PCP in the NAcc, with no significant inhibition after 150 mg/kg, 62% attenuation following 300 mg/kg (p<0.01, T=4.97) and 67% attenuation following 500 mg/kg (p<0.001, T=6.02). PFC DA activity was attenuated 67% after GVG pretreatment (p<0.01, T=3.54), indicating the involvement of cortical GABAergic activity in NMDA-antagonist induced DA release. This data indicates the GABAergic system as a target for pharmacotherapies aimed at NMDA antagonist models of pathophysiology.

EXAMPLE 2

Studies using 11C-raclopride, GVG, and PCP were performed in primates in an effort designed to extend these findings from changes in extracellular DA concentration (in vivo microdialysis) to changes in synaptic concentrations measured by positron emission tomography (PET). PET studies were performed on four Papio anubis baboons. In all cases, prior intravenous administration of 300 mg/kg GVG prevented the diminution of $^{11}$C-ralcopride binding as a consequence of increases in synaptic dopamine following PCP administration (1 mg/kg). The results of this example show that GVG effectively attenuates the elevations in Nacc DA produced by a PCP challenge.

Thus, drugs that selectively target the GABAergic system can be beneficial for the treatment of PCP addiction. More specifically, GVG-induced GABA-T inhibition, which produces an increase in extracellular brain GABA levels, represents an effective drug and novel strategy for the treatment of PCP addiction.

While there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

REFERENCES

Bardo, M. T. (1998) Neurophamacological mechanism of drug reward: beyond dopamine in the nucleus accumbens. Crit. Rev. Neurobiol., 12: 37–67.

Bolser, D. C., Blythin, D. J., Chapman, R. W., Egan, R. W., Hey, J. A., Rizzo, C., Kuo S.-C., Kreutner, W. (1995) The pharmacology of SCH 50911: A novel, orally-active GABA-B receptor antagonist. J. Pharmacol. Exp. Ther., 274: 1393–1398.

Bowery, N. G., Pratt, G. D. (1992) GABAB receptors as targets for drug action Arzneim. Forsch., 42: 215–223.

Brazell, M. P., Mitchell, S. N., Joseph, M. H., Gray, J. A. (1990) Acute administration of nicotine increases the in vivo extracellular levels of dopamine, 3,4-dihydroxyphenylacetic acid and ascorbic acid preferentially in the nucleus accumbens of the rat: Comparison with caudateputamen. Neuropharmacology, 29: 1177–1185.

Chesselet, M.-F. (1984) Presynaptic regulation of neurotransmitter release in the brain: Facts and hypothesis. Neuroscience, 12: 347–375.

Childress, A. R., McLellan, A. T., O'Brien, C. P. (1988) The role of conditioning factors in the development of drug dependence. Psychiatr. Clin. North Amer., 9: 413–426.

Childress, A. R., McLellan, A. T., Ehrman, R. N., O'Brien, C. P. (1986a) Extinction of conditioned responses in abstinent cocaine or opioid users. NIDA Res. Monogr., 76: 189–195.

Childress, A. R., McLellan, A. T., Ehrman, R. N., O'Brien, C. P. (1986b) Classically conditioned responses in abstinent cocaine or opioid users. NIDA Res. Monogr., 76: 24–43).

Clarke, P. B. S., Fibiger, H. C. (1987) Apparent absence of nicotine-induced conditioned place preference. Psychopharmacology, 92: 84–88.

Clarke, P. B. S., Fu, D. S., Jakubovic, A., Fibiger, H. C. (1988) Evidence that mesolimbic dopaminergic activation underlies the locomotor stimulant action of nicotine in animals. J. Pharmacol. Exp. Ther., 246: 701–708.

Damsma, G., Day, J., Fibiger, H. C. (1989) Lack of tolerance to nicotine-induced dopamine release in the nucleus accumbens. Eur. J. Pharmacol., 168: 363–368.

Dewey, S. L., Chaurasia, C. S., Chen, C., Volkow, N. D., Clarkson F. A., Porter, S. P., Straughter-Moore, R. M., Alexoff, D. L., Tedeschi, D., Russo, N. B., Fowler, J. S. and Brodie, J. D. GABAergic attenuation of cocaine-induced dopamine release and locomotor activity. Synapse 25: 393–398, 1997.

Dewey, S. L., Morgan, A. E., Ashby, Jr., C. R., Horan, B., Gardner, E. L., Logan, J., Volkow,. N. D., Fowler, J. S., Kushner, S. A., Brodie, J. D. (1998) A novel strategy for the treatment of cocaine addiction. Synapse, 30: 119–129.

Dewey, S. L., Smith, G. S., Logan, J., Brodie, J. D., Yu, D-W., Ferrieri, R. A., King, P. T., MacGregor, R. R., Martin, T. P., Wolf, A. P., Volkow, N. D., Fowler, J. S. GABAergic inhibition of endogenous dopamine release measured in vivo with 11C-raclopride and positron emission tomography. J. Neuroscience 12,3773–3780, 1992.

Dewey, S. L., Smith, G. S., Logan, J., Brodie, J. D., Fowler, J. S., Wolf, A. P. Striatal binding of the PET ligand 11C-raclopride is altered by drugs that modify synaptic dopamine levels. Synapse 13, 350–356, (1993).

Dewey, S. L., Smith, G. S., Logan, J., Simkowitz, P., Brodie, J. D., Volkow, N. D., Fowler, J. S., Wolf, A. P. (1993) Effects of central cholinergic blockade on striatal dopamine release measured with positron emission tomography (PET) in normal human subjects. Proc. Natl. Acad. Sci., 90: 11816–11820.

Di Chiara, G., Imperato, A. (1988) Drugs abused by humans preferentially increase synaptic dopamine concentrations in the mesolimbic system of freely moving animals. Proc. Natl. Acad. Sci. USA, 85: 5274–5278.

Ehrman, R. N., Robbins, S. J., Childress, A. R., O'Brien, C. P. (1992) Conditioned responses to cocaine-related stimuli in cocaine abuse patients. Psychopharmacology, 107: 523–529.

Fudala, P. J., Iwamoto, E. T. (1986) Further studies on nicotine-induced conditioned place preference. Pharmacol. Biochem. Behav., 25: 1041–1049.

Fudala, P. J., Teoh, K. W., Iwamoto, E. T. (1985) Pharmacologic characterization of nicotine induced conditioned place preference. Pharmacol. Biochem. Behav., 22: 237–241.

Gardner, E. L. (1997) Brain reward mechanisms in Substance Abuse: A Comprehensive Textbook, 3rd end., eds. Lowinson, J. H., Ruiz, P., Millmna, R. B. & Langrod, J. G., 51–85 (Williams and Wilkins, Baltimore, Md., 1997).

Grant, S. M. and Heel, R. C. Vigabatrin: A review of its pharmacodynamic and pharmacokinetic properties, and therapeutic potential in epilepsy and disorders of motor control. Drugs, 41:889–926, 1991.

Henningfield, J. E. (1995) Nicotine medications for smoking cessation. New Eng. J. Med., 333: 1196–1203. 26

Henningfield, J. E., Goldberg. S. R. (1983) Control of behavior by intravenous nicotine injections in human subjects. Pharmacol. Biochem. Behav., 19: 1021–1026.

Henningfield, J. E., London, E. D., Jaffe, J. H. (1987) nicotine reward: studies of abuse liability and physical dependence potential. In: Brain Reward Systems and Abuse, ed. By J. Engel and L. Oreland, New York, Raven Press, pp. 147–164.

Henningfield, J. E., Miyasato, K., D. R. Jasinski (1983) Cigarette smokers self-administer intravenous nicotine. Pharmacol. Biochem. Behav., 19: 887–890.

Horan, P., Smith, M., Gardner, E. Lepore, M., Ashby, Jr. C. R. (1997) (−)-nicotine produces conditioned place preference in Lewis, but not Fischer 344 animals. Synapse, 26: 93–94.

Hurd, Y. L., McGregor, A., Ponten, M. (1997) In vivo amygdala dopamine levels modulate cocaine self-administration behavior in the rat: D1 dopamine receptor involvement. Eur. J. Neuroscience, 12: 2541–2548.

Hurt, R. D., Sachs, D. P., Glover, E. D., Offord, K. P., Johnston, J. A., Dale, L. C., Khayrallah, M. A., Schroeder, D. R., Glover, P. N., Sullivan, C. R., Croghan, I. T., Sullivan, P.M. (1997) A comparison of sustained-release bupropion and placebo for smoking cessation. N. Eng. J. Med., 237: 1195–1202.

Imperato, A., Mulas, A., Di Chiara, G. (1986) Nicotine preferentially stimulates dopamine release in the limbic system of the freely moving rat. Eur. J. Pharmacol., 132: 337-338.

Jarvik, M.., Henningfield, J. E. (1988) Pharmacological treatment of tobacco dependence. Pharmacol. Biochem. Behav., 30: 279–294.

Jung, M. J., Lippert, B., Metcalf, B. W., Bohlen, P., Schechter, P. J. (1977) Gamma-Vinyl GABA (4-amino-hex-5-enoic acid), a new selective irreversible inhibitor of GABA-T: effects on brain GABA metabolism in mice. J. Neurochem., 29: 787–802.

Kerr, D. I. B., Ong, J., Prager, R. H. (1990) GABAB receptor agonists and antagonists. In: GABAB receptors in Mammalian Function, Bowery, N. G., Bittiger, H. and Olpe, H.-R. (eds.) John Wiley and Sons, New York, pp. 29–45.

Kushner, S. A., Dewey, S. L., Kornetsky, C. Comparison of the effects of vigabatrin on cocaine self-administration and food reinforcement. Soc. Neuro. Abstr. 23: 1942 (1997a).

Kushner, S. A., Dewey, S. L., Kometsky, C. The effects of gamma-vinyl GABA on cocaine-induced lowering of brain-stimulation reward thresholds.

Psychopharmacology, 133, 383–388, (1997b).

Lacey, M. G., Mercuri, N. B. and North, A. N. On the potassium conductance increase activated by GABAB and dopamine D2 receptors in rat substantia nigra neurones. J. Physiol. 401: 437–453, 1988.

Logan, J., Fowler, J. S., Volkow, N. D., Wolf, A. P., Dewey, S. L., Schlyer, D. J., MacGregor, R. R., Hitzemann, R., Bendriem, B., Gatley, S. J., Christman, D. R. (1990) Graphical analysis of reversible radioligand binding from time activity measurements applied to [N-$^{11}$C-methyl]-(−)-cocaine PET studies in human subjects. J. Cereb. Blood Flow and Metab., 10: 740–747.

Marshall, D. L., Redfern, P. H., Wonnacott, S. (1997) Presynaptic nicotinic modulation of dopamine release in the three ascending pathways studied by in vivo microdialysis: Comparison of naive and chronic nicotine-treated rats. J. Neurochem., 68: 1511 –1519.

Morgan, A. E., Dewey, S. L. Effects of pharmacologic increases in brain GABA levels on cocaine-induced changes in extracellular dopamine. Synapse 28, 60–65 (1998).

Nisell, M., Nomikos, G. G., Svensson, T. H. (1994a) Systemic nicotine-induced dopamine release in the rat nucleus accumbens is regulated by nicotinic receptors in the ventral segmental area. Synapse, 16: 36–44.

Nisell, M., Nomikos, G. G., Svensson, T. H. (1994b) Infusion of nicotine in the ventral segmental area or the nucleus accumbens differentially affects accumbal dopamine release. Pharmacol. Toxicol., 75: 348–352.

Nisell, M., Nomikos, G. G., Svensson, T. H. (1995) Nicotine dependence, midbrain dopamine systems and psychiatric disorders. Pharmacol. Toxicol., 76: 157–162.

N. R., Van der Kooy, G. F. & Wenger, J. R. Cholecystokinin produces conditioned place-aversion, not place-preferences, in food-deprived rats: evidence against involvement in satiety. Life Sci. 32, 2087–2093, (1989).

O'Brien, C. P., Childress, A. R., McLellan, A. T., Ehrman, R. (1992) A learning model of addiction,. In: Addictive States, O'Brien, C. P. and Jaffe, J. H., (eds), Raven Press, New York, pp. 157–177.

Pontieri, F. E., Tanda, G., Orzi, F., Di Chiara, G. (1997) Effects of nicotine on the nucleus accumbens and similarity to those of addictive drugs. Nature, 382: 255–257.

Porter, R. J., Meldrum, B. S. (1998) Antiepileptic drugs. In: Basic and Clinical Pharmacology, ed. by Katzung, B. G., Appelton and Lange, Stamford, Conn., pp. 386–408.

Roberts, D. C., Andrews, M. M. (1997) Baclofen suppression of cocaine self-administration: demonstration using a discrete trials procedure. Psychopharmacology, 131: 271–277.

Roberts, D. C., Andrews, M. M., Vickers, G. J. (1996) Baclofen attenuates the reinforcing effects of cocaine in animals. Neuropsychopharmacology, 15: 417–423.

Rocha, B. A., Scearce-Levie, K., Lucas, J. J., Hiroi, N., Castanon, N., Crabbe, J. C., Nestler, E. J., Hen, R. (1998) Increased vulnerability to cocaine in mice lacking the serotonin-1B receptor. Nature Neuroscience, 393: 175–178.

Seeman, P., Guan, H. C., Niznik, H. B. (1989) Endogenous dopamine lowers the dopamine D2 receptor density as measured by [3H]raclopride: implications for positron emission tomography of the human brain. Synapse, 3: 96–97.

Sora, I., Wichems, S. I., Takahashi, C., Li, X. F., Zeng, Z., Revay, R., Lesch, K. P., Murphy, D. L., Uhl, D. R. (1998) cocaine reward models: conditioned place preference can be established in dopamine- and serotonin-transporter knock-out mice. Proc. Natl. Acad. Sci., U.S.A., 95: 7699–7704.

Takada, K., Yanagita, T. (1997) Drug dependence study on vigabatrin in rhesus monkeys and animals. Arzneim-Forsch Drug Res.47: 1087–1095.

Tsuji M, Nakagawa Y, Ishibashi Y, Yoshii T, Takashima T, Shimada M, Suzuki T. (1995) Activation of ventral segmental GABA-B receptors inhibits morphine-induced place preference in animals. Eur. J. Pharmacol., 313: 169–173.

Valentine, J. D., Hokanson, J. S., Matta, S. G., Sharp, B. M. (1997) Self-administration in animals allowed unlimited access to nicotine. Psychopharmacology, 133: 300–304.

Van Der Kooy, K. (1987). In Methods of Assessing the Properties of Abused Drugs, M. A. Bozarth, Ed., Springer-Verlag, New York, pp. 229–241.

Volkow, N. D., Wang, G. J., Fowler, J. S., Logan, J., Schlyer, D., Hitzemann, R., Liberman, J., Angrist, B., Pappas, N., MacGregor, R., Burr, G., Cooper, T., Wolf, A. P. Imaging endogenous doparnine competition with [11C] raclopride in the human brain. Synapse, 16, 255–262 (1994).

Wikler, A. (1965) Conditioning factors in opiate addiction and relapse. In: Narcotics, Kassenbaum, G. G. and Wilner, D. I. (eds), McGraw-Hill, New York, pp. 85–100.

What is claimed is:

1. A method for changing addiction-related behavior of a mammal suffering from PCP addiction which comprises administering to the mammal an effective amount of gamma vinylGABA (GVG) or a pharmaceutically acceptable salt thereof, or an enantiomer or a racemic mixture thereof, wherein the effective amount is sufficient to diminish, inhibit or eliminate behavior associated with craving or use of PCP.

2. The method of claim 1, wherein said elimination of behavior associated with craving of drugs of abuse occurs in the absence of an aversive response or appetitive response to GVG.

3. The method of claim 1, wherein GVG is administered in an amount of about 15 mg/kg to about 600 mg/kg.

4. The method of claim 1, wherein said addiction related behavior is conditioned place preference.

5. The method of claim 1, wherein said mammal is a primate.

6. A method for changing addiction-related behavior of a mammal suffering from PCP addiction which comprises administering to the mammal an effective amount of gamma vinylGABA (GVG) or a pharmaceutically acceptable salt thereof, or an enantiomer or a racemic mixture thereof, wherein the effective amount attenuates the rewarding/incentive effects of PCP in the absence of altering rewarding/incentive effects of food in said mammal.

7. The method of claim 6, wherein the rewarding/incentive effects of drugs of abuse is attenuated in the absence of an alteration in the locomotor function of said mammal.

8. The method of claim 6, wherein said mammal is a primate.

9. A method of ameliorating effects of PCP addiction which comprises administering to a mammal an effective amount of gamma vinylGABA (GVG) or a pharmaceutically acceptable salt thereof, or an enantiomer or a racemic mixture thereof, wherein the effective amount is sufficient to reduce PCP dependency characteristics.

10. The method of claim 9, wherein GVG is administered in an amount from about 15 mg/kg to about 600 mg/kg.

11. The method of claim 9, wherein said PCP dependency characteristics are reduced in the absence of an aversive response or appetitive response to GVG.

12. The method of claim 9, wherein said PCP dependency characteristics are reduced in the absence of an alteration in the locomotor function of said mammal.

13. The method of claim 9, wherein said mammal is a primate.

14. A method for changing addiction-related behavior of a mammal suffering from PCP addiction which comprises administering to the mammal an effective amount of gabapentin, wherein the effective amount is sufficient to diminish, inhibit or eliminate behavior associated with craving or use of PCP.

15. The method of claim 14, wherein the gabapentin is administered in an amount of about 500 mg to about 2 g/day.

16. A method for changing addiction-related behavior of a mammal suffering from PCP addiction which comprises administering to the mammal an effective amount of topirimate, wherein the effective amount is sufficient to diminish, inhibit or eliminate behavior associated with craving or use of PCP.

17. The method of claim 16, wherein the topiramate is administered in an amount of about 50 mg to about 1 g/day.

18. A method for changing addiction-related behavior of a mammal suffering from PCP addiction which comprises administering to the mammal an effective amount of progabide, wherein the effective amount is sufficient to diminish, inhibit or eliminate behavior associated with craving or use of PCP.

19. The method of claim 18, wherein the progabide is administered in an amount of about 250 mg to about 2 g/day.

20. A method for changing addiction-related behavior of a mammal suffering from PCP addiction which comprises administering to the mammal an effective amount of fengabine, wherein the effective amount is sufficient to diminish, inhibit or eliminate behavior associated with craving or use of PCP.

21. The method of claim 20, wherein the fengabine is administered in an amount of about 250 mg to about 4 g/day.

22. A method for changing addiction-related behavior of a mammal suffering from PCP addiction which comprises administering to the mammal an effective amount of gamma-hydroxybutyric acid, wherein the effective amount is sufficient to diminish, inhibit or eliminate behavior associated with craving or use of PCP.

23. The method of claim 22, wherein the gamma-hydroxybutyric acid is administered in an amount of about 5 mg/kg to about 100 mg/kg/day.

24. A method of ameliorating effects of PCP addiction which comprises administering to a mammal an effective amount of gabapentin, wherein the effective amount is sufficient to reduce PCP dependency characteristics.

25. The method of claim 24, wherein the gabapentin is administered in an amount of about 500 mg to about 2 g/day.

26. A method of ameliorating effects of PCP addiction which comprises administering to a mammal an effective amount of topiramate, wherein the effective amount is sufficient to reduce PCP dependency characteristics.

27. The method of claim 26, wherein the topiramate is administered in an amount of about 50 mg to about 1 g/day.

28. A method of ameliorating effects of PCP addiction which comprises administering to a mammal an effective amount of progabide, wherein the effective amount is sufficient to reduce PCP dependency characteristics.

29. The method of claim 28, wherein the progabide is administered in an amount of about 250 mg to about 2 g/day.

30. A method of ameliorating effects of PCP addiction which comprises administering to a mammal an effective amount of fengabine, wherein the effective amount is sufficient to reduce PCP dependency characteristics.

31. The method of claim 30, wherein the fengabine is administered in an amount of about 250 mg to about 4 g/day.

32. A method of ameliorating effects of PCP addiction which comprises administering to a mammal an effective amount of gamma-hydroxybutyric acid, wherein the effective amount is sufficient to reduce PCP dependency characteristics.

33. The method of claim 32, wherein the gamma-hydroxybutyric acid is administered in an amount of about 5 mg/kg to about 100 mg/kg/day.

* * * * *

UNITED STATES PATENT AND TRADEMARK OFFICE
CERTIFICATE OF CORRECTION

PATENT NO. : 6,395,783 B1
DATED : August 7, 2002
INVENTOR(S) : Dewey et al.

It is certified that error appears in the above-identified patent and that said Letters Patent is hereby corrected as shown below:

<u>Title page,</u>
Item [57], ABSTRACT,
Line 3, now reads "addiction to phencyclidine (PCP).", should read -- addiction to hallucinogenic drugs, preferably phencyclidine (PCP). --

<u>Column 8,</u>
Line 33, now reads "$mMC1^{31}$", should read -- $mMC1^-$ --

<u>Column 9,</u>
Line 45, now reads "Neurophamacological", should read -- Neuropharmacological --

<u>Column 11,</u>
Line 53, now reads "Kometsky", should read -- Kornetsky --

Signed and Sealed this

Twenty-ninth Day of October, 2002

*Attest:*

*Attesting Officer*

JAMES E. ROGAN
*Director of the United States Patent and Trademark Office*